United States Patent [19]

Isowa et al.

[11] 4,116,768

[45] Sep. 26, 1978

[54] PROCESS FOR PRODUCING A PEPTIDE

[75] Inventors: Yoshikazu Isowa; Muneki Ohmori, both of Tokyo; Hideaki Kurita, Sagamihara; Tetsuya Ichikawa, Sagamihara; Masanari Sato, Sagamihara; Kaoru Mori, Sagamihara; Kiyotaka Oyama, Sagamihara, all of Japan

[73] Assignee: (Zaidanhojin) Sagami Chemical Research Center, Tokyo, Japan

[21] Appl. No.: 839,848

[22] Filed: Oct. 6, 1977

Related U.S. Application Data

[60] Division of Ser. No. 803,350, Jun. 3, 1977, which is a continuation of Ser. No. 734,010, Oct. 19, 1976, abandoned.

[30] Foreign Application Priority Data

Apr. 19, 1976 [JP] Japan .................... 51-43686

[51] Int. Cl.² .............................................. C12D 13/06
[52] U.S. Cl. ................................. 195/29; 260/112.5 R
[58] Field of Search ............................................ 195/29

[56] References Cited

U.S. PATENT DOCUMENTS

| 3,803,327 | 4/1974 | Fujimaki et al. | 195/29 X |
| 3,888,837 | 6/1975 | Tsumita et al. | 260/112.5 |
| 3,972,773 | 8/1976 | Isowa et al. | 195/29 |

OTHER PUBLICATIONS

Journal of Biological Chemistry, vol. 204, pp. 891 to 902, (1953).

Journal of Biological Chemistry, vol. 185, pp. 629 to 641, (1950).
Biochemical & Biophysical Research Communications, vol. 21, No. 3, pp. 242 to 256, (1965).
Methods in Enzymology, vol. 19, pp. 883 to 889.

*Primary Examiner*—Lionel M. Shapiro
*Attorney, Agent, or Firm*—Oblon, Fisher, Spivak, McClelland & Maier

[57] ABSTRACT

A peptide having the formula

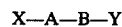

wherein A and B are the same or different and represent an amino acid residue or a peptide residue; X represents an amino protective group and Y represents a carboxyl protective group, is prepared by reacting an amino acid or peptide having an N-terminal protective group or a salt thereof of the formula:

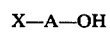

with an amino acid or peptide having a C-terminal protective group or a salt thereof of the formula:

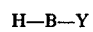

in the presence of metalloproteinase in an aqueous solution having a pH which maintains the enzyme activity of said metalloproteinase.

3 Claims, No Drawings

PROCESS FOR PRODUCING A PEPTIDE

This is a division of application Ser. No. 803,350, filed June 3, 1977 which in turn is a continuation of Ser. No. 734,010 filed Oct. 19, 1976, now abandoned.

BACKGROUND OF THE INVENTION

1. Field of the Invention

The present invention relates to a process for producing a peptide. More particularly, the invention relates to a process for producing a peptide by using a specific enzyme as a catalyst.

2. DESCRIPTION OF THE PRIOR ART

Conventional processes for producing peptides include the azide method, the mixed acid anhydride method, the carbodiimide method, the active ester method, the acid chloride method and the like. However, various industrial problems are encountered by the conventional processes, such as that racemization of the carboxyl component at the C-terminal amino acid residue occurs. Other problems include side reactions, temperature control, selection of solvent, the properties of the amino protective groups and the carboxyl protective groups and the effects of functional groups on the side chains of amino acids. In the fragment condensation method of preparing a peptide, a peptide can be divided for each fragment so as to minimize the damage caused by accidental failure and thus, the method has several industrial advantages. The fragment condensation method can be advantageously applied to compounds containing glycine (the only amino acid which can not be racemized) at the carboxyl terminal group. However, for compounds containing any other amino acid at the carboxyl terminal group, racemization cannot be prevented. In actuality, in any peptide synthesis, the racemization problem is serious. When racemization occurs, the purity of the product is decreased and it is necessary to separate the impure isomer from the product. This is very detrimental for any industrial operation.

Among the conventional methods for forming peptide bonds, the azide method is the only method in which racemization is not much of a problem, and it is for this reason that it is a desirable method. However, since the azide method involves complicated operational procedures, and because an urea derivative is produced in a side reaction thereby decreasing the yield of product, the azide method is also unsatisfactory.

In addition to the various organic chemical processes, for preparing peptides, a particular peptide synthesis using the enzyme papain or chymotrypsin has been disclosed (see, for example, J. S. Fruton "Advances in Protein Chemistry", 5, Academic Press Inc., New York, N.Y. 1949). The reactions of this method are as follows.

(1) Bz—Leu—OH + H—Leu—NH φ
     (I)         (II)

 Bz—Leu—Leu—NH φ
             (III)

(2) Bz—Leu—OH + H—Gly—NH φ
     (I)         (II)

 Bz—Leu—Gly—NH φ
             (III)

(3) Bz—Tyr—OH + H—Gyl—NH φ
     (I)         (II)

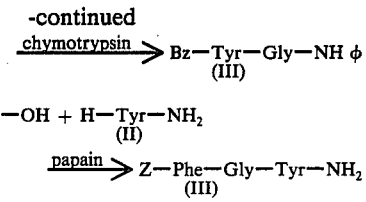

(4) Z—Phe—Gly—OH + H—Tyr—NH₂
     (I)              (II)

 Z—Phe—Gly—Tyr—NH₂
                (III)

The problem which is common to reactions (1) to (3) is that it is necessary to remove the phenylamino group from the peptide (III) by severe conditions because the phenyl amino group which is bonded to the C-terminal group of the amine component (II) cannot be easily separated from the peptide and thus cleavage of the peptide chain is disadvantageous. Because of this deficiency, this mode of peptide synthesis cannot be practically used for peptide synthesis. On the other hand, reaction (4) is accompanied by transamidation and transpeptidation side reactions and thus is not practically suitable. (See, for example, R. B. Johnston et al; J. Biol, Chem., 185, 629 (1950) and J. S. Fruton et al; J. Biol., Chem., 204, 891 (1953).) In reaction (4), the primary amino group of the acid amide bonded to the terminal group of the amine component, promotes the papain catalyzed amidase reaction. Accordingly, these processes provide only a theoretical interest in showing that papain and chymotrypsin act as catalysts for the synthesis of peptide bonds in which the phenylamino or a primary amino group is used as the protective group for the terminal carboxyl group of the amine component. These processes give no indication of the possibility of synthesizing a desired oligopeptides or polypeptides.

SUMMARY OF THE INVENTION

Accordingly, one object of the present invention is to provide a process for synthesizing a desired oligopeptide or polypeptide by a simple operation in high yield.

Briefly, this and other objects of the invention as hereinafter will become more readily apparent can be attained in a process for producing a peptide having the formula

X—A—B—Y wherein A and B are the same or different and represent an amino acid residue or a peptide residue, X represents an amino protective group and Y represents a carboxyl protective group by reacting an amino acid or peptide having an N-terminal protective group or a salt thereof of the formula

X—A—OH with an amino acid or peptide having a C-terminal protective group or a salt thereof of the formula

H—B—Y in the presence of metalloproteinase in an aqueous solution having a pH which maintains the enzyme activity of said metalloproteinase.

DETAILED DESCRIPTION OF THE PREFERRED EMBODIMENTS

The metalloproteinase enzymes used in the present invention include the enzymes produced from microorganisms such as Bacillus subtilis, Bacillus thermoproteoliticus, Streptomyces caespitosus, Bacillus megaterium, Bacillus polymyxa, Streptomyces griseus, Streptomyces naraensis, Streptomyces fradiae, Tseudomonas aeruginosa, Aspergillus oryzae, Clostridium histolyticum, Proteus aeruginosa and the like. (Prolisin, Thermolysin, Collagenase, Thermoase, Tacynase N, Pronase) It has been reported that these enzymes hydrolyze peptide bonds involving the amino groups of hydrophobic amino acid residues such as leucine, isoleucine, phenylalanine and valine. (H. Matsubara et al, Biochem. Biophys. Res. Comm. 21, 242 (1965). The amino acid or peptide starting materials having the formula

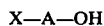

wherein X represents a protective group for the terminal amino group and A represents an amino acid residue or a peptide residue, which are used in the process of the invention, are hereinafter referred to as the acid component. The radical A in the formula more definitively represents an amino acid residue or peptide residue wherein suitable amino acids include aliphatic amino acids such as monoamino monocarboxylic acids e.g., glycine (Gly), alanine (Ala), valine (Val), norvaline (nor-Val), leucine (Leu), isoleucine (iso-Leu), norleucine (nor-Leu); oxyamino acids e.g. serine (Ser), threonine(Thr), homo-serine(homo-Ser); sulfur-containing amino acids, e.g., methionine(Met) or cystine (CysS) and cysteine(CysH); monoamino dicarboxylic acids, e.g. aspartic acid (Asp), glutamic acid (Glu), asparagine (Asn) and glutamine (Gln); diamino monocarboxylic acids, e.g. ornithine (Orn), lysine (Lys), arginine (Arg); aromatic amino acids, e.g. phenylalanine (Phe), tyrosine (Tyr) and heterocyclic amino acids, e.g. histidine (His), tryptophan (Trp). (The amino acids are designated by symbols which are commonly used in the field. The peptides are also designated by combinations of these symbols).

Suitable protective groups for the free terminal amino group (an N-terminal protective group) of the acid component include tertiary alkoxycarbonyl groups such as t-butyloxycarbonyl (BOC—), t-amyloxycarbonyl (t-Aoc); benzyoxycarbonyl groups which can be substituted with an inert substituent, such as benzyloxycarbonyl (Z—), p-methoxybenzyloxycarbonyl (PMZ—), 3,5-dimethoxybenzyloxycarbonyl (Z(O-Me)$_2$—), 2,4,6-trimethylbenzyloxycarbonyl (TMZ—), p-phenylazobenzyloxycarbonyl (PZ—); p-toluenesulfonyl (tos—); o-nitrophenyl sulfenyl (Nps—), and the like.

The amino acid or peptide starting materials having the formula

which are used in the process of the invention, are referred as the amine component. In the formula B represents an amino acid residue or peptide residue which can be the same defined above as A. The protective groups for the carboxyl group (C-terminal protective groups) of the amine component include alkoxy groups such as methoxy (—OMe), ethoxy (—OEt); tertiary alkoxy groups such as t-butoxy (—O-t-Bu); and benzyloxy groups which can be substituted such as benzyloxy (—OBzl), p-nitrobenzyloxy (—OBzl (p-NO$_2$) ), benzhydryloxy (—OBzh), benzylamino (—NHBzl), 2,4-dimethoxybenzylamino (—NHDMB), benzhydrylamino (—NHBzh) or unsubstituted amino (—NH$_2$) etc.

The acid component and the amine component which are the reactants in the process of the invention include amino acid residues and peptide residues which have a functional group on the side chain. In most cases, it is preferable to protect the functional group with a protective group. Suitable protective groups for ω-amino groups (N$^\omega$) include N$^\omega$-benzyloxycarbonyl (N$^\omega$-Z), t-butoxycarbonyl (N$^\omega$-BOC) and tosyl (N$^\omega$-Tos). Suitable protective groups for N-guanidino groups (N$^G$) of Arg include nitro (N$^G$-NO$_2$), N$^G$-benzyloxycarbonyl (N$^G$-Z) and N$^G$.N$^G$-dibenzyloxycarbonyl (N$^G$-Z-Z). Suitable protective groups for imizadole ring (N$^{im}$) include N$^{im}$-benzyl (N$^{im}$-Bzl) and tosyl (N$^{im}$-tos). Suitable protective groups for ω-carboxyl groups include ω-benzyloxy (-OBzl). Suitable protective groups for the hydroxyl groups of aliphatic or aromatic oxyamino acids include aralkyl groups such as benzyl (Bzl). Suitable protective groups for the mercapto group of CysH include benzyl (Bzl). The protective groups should possess the characteristics of being stable in the main reaction and that they can be easily separated from the product without being involved in side-reaction.

The acid component and the amine component starting materials can have protective groups, and the N$^\alpha$-amino group of the amine component can be free or in the form of an inorganic or organic salt such as a hydrochloride, hydrobromide, oxlate, p-toluenesulfonate or acetate. In the process of the invention, the condensation reaction in which the peptide bond can be formed is conducted in an aqueous solution having a pH which maintains enzyme activity of about 6 to 8.

There are two methods which can be employed to achieve the proper pH to maintain enzyme activity. One method is to conduct the condensation reaction in a buffer solution such as a citric acid buffer solution, McIlvaine buffer solution, Kolthoff buffer solution, Michaelis' buffer solution, tris buffer solution or Clark-Lub's buffer solution in which the acid component and amine component are dissolved and the enzyme is added. The other method is to conduct the condensation reaction by maintaining the pH of the reaction mixture in the proper range to maintain enzyme activity by adding the acid or the base to the reaction mixture depending upon the pH detected.

The starting materials are usually used in a ratio of 0.8 to two moles, preferably one to 1.5 moles of the acid component per one mole of the amine component. If the starting materials are not too soluble in the aqueous medium, it is possible to improve the solubility of the reactants by adding a solvent such as an alcohol, e.g., methanol, or ethanol; dimethylformamide; dioxane; tetrahydrofuran, dimethylsulfoxide or the like to the aqueous solution. The amount of the added solvent should be limited so as not to inhibit the activity of the enzyme in the reaction of the invention. If a solvent is employed, it is usually used in an amount of less than 1 part by weight, peferably, 0.2 to 1.0 part by weight per one part by weight of water. The reaction of the invention is performed in an aqueous medium, and it is necessary to decrease the relative solubility of the reaction product preferably to a sparingly soluble or insoluble state in the system.

In the reaction of the invention, a catalytic amount of an enzyme is employed, preferably 10~500 mg of enzyme per 1 mmole of the amine component. When a purified enzyme is used, the amount of the enzyme can be 5 to 30 mg. The reaction temperature is usually in a range of 20° to 80° C., preferably 20° to 50° C. in order to maintain enzyme activity. The reaction proceeds smoothly under these conditions for 1 to 24 hours. The reaction product precipitates from the reaction system and the reaction product can be easily isolated.

The reaction in the presence of the metallo proteinase enzyme catalyst is illustrated as follows.

When a dipeptide is produced by the reaction:
BOC-Tyr(Bzl)-OH + H-Val-NHDMB → BOC-Tyr(Bzl)-Val-NHDMB
BOC-His(Bzl)-OH + H-Leu-NHDMB → BOC-His(Bzl)-Leu-NHDMB
wherein the amide derivative, i.e. Val and Leu is used as the amine component and the BOC derivative, i.e. Tyr and His whose side chain is protected, is used as the acid component, the condensation products are obtained in a yield of about 60%. Examples of the condensation of acyl amino acids and amino acid amides are shown in Table 1. Examples of the condensation of acyl amino acids and dipeptide amides are shown in Table 2. Examples of the condensation of acyl dipeptides and amino acid amides are shown in Table 3. Examples of the condensation of acyl dipeptides and dipeptide amides are shown in Table 4. Examples of the condensation of acylamino acid and dipeptide esters are shown in Table 5.

When the metalloproteinase is used as the enzyme catalyst, amino acids having special characteristics are very reactive as the amine component, and various amino acids can be used in the form of an acylamino acid or an acyl peptide as the acid component, as shown in the following tables. It is clear that the metalloproteinase can be used in the synthesis of peptides by using hydrophobic amino acids such as Leu, iso-Leu, Val, Phe, and the like, as the N-terminal amino acid of the amine component.

In another embodiment of the present invention a protein proteinase inhibitor from e.g., potato is used. Commercial crude metalloproteinases generally include alkaline proteinases which have an optimum pH on the alkali side and hydrolyze non-substituted amides and amino acids or peptides esters consisting of primary alcohol. For example, prolisin comprises a metalloproteinase having no esterase or amidase activity and an alkaline proteinase in a ratio of 7:3. The other components of prolisin comprise a small amount of amylase, protein and about 65% of an excipien of starch. Accordingly, when Prolisin is used as the catalyst to form peptide bonds, the esters formed by reaction of a carboxyl group and a primary alcohol, such as a methyl ester or an ethyl ester are not suitable as the protective group for the carboxyl group, nor is an un-substituted amide. Accordingly, more complicated protective groups are required in addition to complicated operations and expensive reagents (alcohols and amines). When an alkaline proteinase is removed from Prolisin, complicated operations are also required which is disadvantageous. It has now been found that the yield of the desired products can be substantially improved by adding an inhibitor for the proteolytic enzyme (proteinase) in the syntheses of peptides using the metalloproteinase, particularly the crude metalloproteinase.

One embodiment of the invention can be achieved when it is considered that the enzyme of the metalloproteinase has a catalytic action on the condensation reaction wherein peptide bonds are formed and the activity of alkaline proteinase included in a commercial enzyme which principally contains the metallo proteinase can be inhibited by using an inhibitor to the proteolytic enzyme. Suitable inhibitors for the proteolytic enzyme used in the invention can be extracted from oats, fava, kidney beans and the potato. The method of extraction is disclosed in Nippon Nogei Kagaku Kaishi, 31, page 38 (1957). The inhibitor used in the invention need not be a pure material, but can be a crude extract. When the inhibitor is added, it is possible to use an amine component having a primary alkoxy group, e.g. a methoxy group (O-Me), an ethoxy group (—OEt) or an unsubstituted amino group as the protective group for the carboxyl group.

In another embodiment of the invention an acid component (I) can be reacted with an amine component (II) in the combination of (a) the combination of L-I and DL-II, (b) the combination of DL-I and L-II, or (c) the combination of DL-I and DL-II to produce an L,L-acyl dipeptide. For example, the acid component (I) can be a compound having the formula

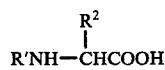

wherein R' represents an acyl group and $R^2$ represents a side chain group of an α-amino acid. The amine component (II) can be a compound having the formula

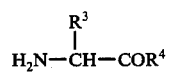

wherein $R^3$ represents a side chain group of an α-amino acid and $R^4$ represents a protective group for the carboxyl group. In this embodiment, at least one of the acid component(I) or the amine component (II) can be a racemic compound whereas the L,L-acyl dipeptide can be selectively produced by using the metalloproteinase in the reaction. Preferably, an inhibitor is added to the proteolytic enzyme.

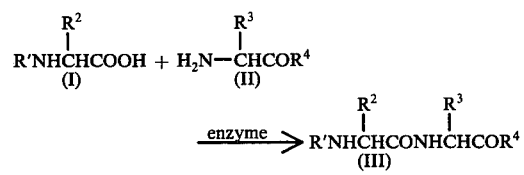

wherein R' represents an acyl group; $R^2$ represents a side chain group of an α-amino acid, $R^3$ represents a side chain group of an α-amino acid and $R^4$ represents a protective group for the carboxyl group. Three combinations of the acid component (I) and the amine component (II) can be set forth as follows:

The products are LL-III, because the reaction is selective. Compounds of formulae I and II are easily obtained. In accordance with the process of the invention, aspartyl phenylalanine methyl ester which is known as a sweetener can be easily produced by reducing N-benzyloxycarbonyl-(β-benzyl)-aspartyl phenylalanine methyl ester produced by the reaction of N-benzyloxycarbonyl-(β-benzyl)aspartic acid with phenylalanine methyl ester. Only a catalytic amount of enzyme is enough and the enzyme can be repeatedly used. The reaction smoothly proceeds under mild conditions in a buffer solution or a solution having a desired pH. The yields are relatively high and the purity of the product is substantially high. The process of the invention can be applied to the stepwise extension of a peptide chain and also for fragmented condensation reactions which are effective for industrial purposes, without racemization which can not be attained by the conventional methods.

Having generally described the invention, a more complete understanding can be obtained by reference to certain specific examples which are included for purposes of illustration only and are not intended to be limiting unless otherwise specified.

In the examples, the purified thermoase was produced by dissolving a crude thermoase in 1/50 M-calcium acetate aqueous solution and separating the insoluble material by centrifugal separation and dialyzing the supernatant twice with 1/100 M-calcium acetate aqueous solution. Thereafter, 0.8 times the amount of acetone was added to the dialyzed solution, and the precipitate was filtered. Acetone was added to the filtrate to 2.5 times the amount of the filtrate, and the precipitate was separated by centrifugal separation and dried under reduced pressure at normal temperature.

EXAMPLE 1

A 40 ml amount of McIlvaine buffer solution having a pH of 7.5 was added to 817 mg (2.20 mmol) of BOC-Tyr(Bzl)-OH and 606 mg (2.00 mmol) of H-Val-NHDMB.HCl and then 2.0 ml of 1N NaOH was added to the solution. Then, 200 mg of neutral proteinase (Streptomyces; titre of 100 units/mg manufactured by Kyowa Hakko K.K.) was added to the mixture with stirring at 38° C. for 24 hours and the reaction was conducted. The resulting colorless precipitate was filtered and was sequentially washed with water, 0.5 N HCl, 7% ammonia water and water whereby 1.08 g of crude crystals was obtained. The product was dissolved in 200 ml of a hot ethanol, and the hot solution was treated with activated carbon for 30 minutes to remove protein. The solution was concentrated and water was added to the residue whereby a crystalline product of BOC-Tyr (Bzl)-Val-NHDMB was obtained.

| yield | 700 mg(56%) | | |
|---|---|---|---|
| melting point | 183 to 185° C | | |
| $[\alpha]_D^{25} = -1.6°$ (0=1.0 chloroform) | | | |
| Elemental Analysis | C | H | N |
| Calculated (%) | 67.83 | 7.32 | 6.78 |
| Found (%) | 67.71 | 7.35 | 6.06 |

EXAMPLE 2

A 40 ml amount of McIlvaine buffer solution having a pH of 7.5 was added to 760 mg (2.20 mmol) of BOC-His(Bzl)-OH and 634 mg (2.00 mmol) of H-Leu-NHDMB.HCl and then 1N NaOH was added to the solution. Then, 200 mg of neutral proteinase (Streptomyces) was added to the mixture with stirring at 38° C. for 24 hours and the reaction was conducted. The resulting colorless precipitate was filtered and was sequentially washed with water, 7% ammonia and water whereby 1.01 g of crude crystals were obtained. The product was dissolved in 200 ml of hot ethanol and the hot solution was treated with activated carbon for 30 minutes to remove protein. The solution was concentrated and water was added to the residue whereby a crystalline product of BOC-His(Bzl)-Leu-NHDMB.H$_2$O was obtained.

| yield | 800 mg (64%) | | |
|---|---|---|---|
| melting point | 144 to 146° C | | |
| $[\alpha]_D^{25} = 0.69°$ (0 = 1.0 chloroform) | | | |
| Elemental Analysis: | C | H | N |
| Calculated (%) | 63.34 | 7.57 | 11.19 |
| Found (%) | 63.37 | 7.45 | 11.17 |

EXAMPLES 3 to 37:

The process of Example 1 was repeated except that the acid components and the amine components shown in Tables 1 to 5 were used. In Table 1, the acid components were Nα-acyl amino acids and the amine components were amino acid amides. In Table 2, the acid components were Nα-acyl amino acids and the amine components were dipeptide amides. In Table 3, the acid components were Nα-acyl dipeptides and the amine component was H-Leu-NHBzh. In Table 4, the acid components were Nα-acyl dipeptides and the amine components were dipeptide amide of H-Phe-Ala-NHBzh. In Table 5, the acid components were Nα-acyl amino acids and the amine components were dipeptide esters.

Table 1

| Ex. | Acid component | Amine component | Product | Yield (%) | Melting point (° C) | | Elementary Analysis calculated (%) found (%) | | |
|---|---|---|---|---|---|---|---|---|---|
| | | | | | | | C | H | N |
| 3 | Z—Leu—OH | H—Phe—NHBzh | Z—Leu—Phe—NHBzh | 69 | 233 14 224 | 1 | 74.84 | 6.80 | 7.27 |
| | | | | | | 2 | 74.72 | 6.79 | 7.30 |
| 4 | Z—Phe—OH | H—Phe—NHBzh | Z-Phe—Phe—NHBzh | 48 | 204–205 | 1 | 76.57 | 6.10 | 6.87 |
| | | | | | | 2 | 76.32 | 6.05 | 6.93 |
| 5 | Z—Gln—OH | H—Phe—NHBzh | Z—Gln—Phe—NHBzh . ½H$_2$O | 91 | 260–263 | 1 | 69.86 | 6.20 | 9.31 |
| | | | | | | 2 | 69.64 | 6.00 | 9.14 |
| 6 | Z—Arg(NO$_2$)—OH | H—Phe—NHBzh | Z—Arg(NO$_2$)—Phe—NHBzh | 48 | 214–216 | 1 | 64.95 | 5.90 | 14.73 |
| | | | | | | 2 | 64.61 | 5.71 | 14.78 |
| 7 | Z—Trp—OH | H—Phe—NHBzh | Z—Trp—Phe—NHBzh . ½H$_2$O | 34 | 191–194 | 1 | 74.63 | 5.96 | 8.49 |
| | | | | | | 2 | 75.04 | 5.91 | 8.59 |
| 8 | Z—Pro—OH | H—Phe—NHBzh | Z—Pro—Phe—HNBzh | 44 | 186–189 | 1 | 74.84 | 6.28 | 7.43 |
| | | | | | | 2 | 74.74 | 6.25 | 7.55 |
| 9 | Z—Phe—OH | H—Val—NHBzh | Z—Phe—Val—NHZzh | 51 | 230–233 | 1 | 74.54 | 6.62 | 7.46 |
| | | | | | 2 | 74.65.67 | 7.49 | | |
| 10 | Z—Phe—OH | H—Leu—NHBzh | Z—Phe—Leu—NHBzh | 57 | 203–207 | 1 | 74.84 | 6.80 | 7.27 |
| | | | | | | 2 | 74.62 | 6.78 | 7.27 |
| 11 | Z—Phe—OH | H—Ile—NHBzh | A—Phe—Ile—NHBzh 13 H$_2$O | 30 | 207–212 | 1 | 72.58 | 6.94 | 7.05 |

Table 1-continued

| Ex. | Acid component | Amine component | Product | Yield (%) | Melting point (°C) | 1 2 | Elementary Analysis calculated (%) found (%) C | H | N |
|---|---|---|---|---|---|---|---|---|---|
| | | | | | | 2 | 72.99 | 6.70 | 7.17 |

Table 2

| Ex. | Acid component | Amine component | Product | Yield (%) | Melting point (°C) | 1 2 | Elementary Analysis calculated (%) found (%) C | H | N |
|---|---|---|---|---|---|---|---|---|---|
| 12 | Z—Phe—OH | H—Phe—Arg(NO₂)—NHBzh | Z—Phe—Phe—Arg(NO₂)—NHBzH . H₂O | 78 | 72–76 | 1 | 65.04 | 6.07 | 13.49 |
| | | | | | | 2 | 65.03 | 5.82 | 13.55 |
| 13 | Z—Leu—OH | H—Ala—Phe—NHBzh | Z—Leu—Ala—Phe—NHBzh . H₂O | 33 | 162–165 | 1 | 70.05 | 6.95 | 8.40 |
| | | | | | | 2 | 70.21 | 6.80 | 8.23 |
| 14 | Z—Phe-13 OH | H—Ala—Phe—NHBzh | Z—Phe—Ala—Phe—NHBzh . H₂O | 23 | 173–175 | 1 | 71.98 | 6.33 | 8.00 |
| | | | | | | 2 | 71.65 | 6.38 | 7.82 |
| 15 | Z—Phe—OH | H—Phe—Ala—NHBzh | Z—Phe—Phe—Ala—NHBzH-½H₂O | 25 | 205–209 | 1 | 72.91 | 6.26 | 8.10 |
| | | | | | | 2 | 72.89 | 6.18 | 8.18 |
| 16 | Z—Phe—OH | H—Leu—Gly—NHBzh | Z—Phe—Leu—Gly—NHBzh-½H₂O | 31 | 207–208 | 1 | 70.89 | 6.73 | 8.70 |
| | | | | | | 2 | 70.84 | 6.60 | 8.82 |

Table 3

| Ex. | Acid component | Amine component | Product | Yield (%) | Melting point (°C) | 1 2 | Elementary Analysis calculated (%) found (%) C | H | N |
|---|---|---|---|---|---|---|---|---|---|
| 17 | Z—Trp—Gly—OH | H—Leu—NHBzh | Z—Trp—Gly—Leu—NHBzh | 19 | 183–185 | 1 | 71.30 | 6.43 | 10.40 |
| | | | | | | 2 | 70.92 | 6.39 | 10.45 |
| 18 | PMZ—Ala—Ala—OH | H—Leu—NHBzh | PMZ—Ala—Ala—Leu—NHBzh | 51 | 236–239 | 1 | 67.75 | 7.02 | 9.30 |
| | | | | | | 2 | 68.02 | 7.05 | 9.42 |
| 19 | Z—Leu—Ala—OH | H—Leu—NHBzh | Z—Leu—Ala—Leu—NHBzh | 46 | 228–232 | 1 | 70.33 | 7.54 | 9.11 |
| | | | | | | 2 | 70.52 | 7.48 | 8.93 |
| 20 | Z—Phe—Ala—OH | H—Leu—NHBzh | Z—Phe—Ala—Leu—NHBzh | 51 | 240–241 | 1 | 72.20 | 6.84 | 8.64 |
| | | | | | | 2 | 72.14 | 6.84 | 8.85 |
| 21 | Z—Ala—Leu—OH | H—Leu—NHBzh | Z—Ala—Leu—Leu—NHBzh | 38 | 225–226 | 1 | 70.33 | 7.54 | 9.11 |
| | | | | | | 2 | 70.14 | 7.52 | 9.33 |
| 22 | Z—Ala—Phe—OH | H—Leu—NHBzh | Z—Ala—Phe—Leu—NHBzh | 87 | 202–205 | 1 | 72.20 | 6.84 | 8.64 |
| | | | | | | 2 | 72.27 | 6.82 | 8.88 |

Table 4

| Ex. | Acid components | Amine component | Product | Yield (%) | Melting point (°C) | 1 2 | Elementary Analysis calculated (%) found (%) C | H | N |
|---|---|---|---|---|---|---|---|---|---|
| 23 | Z—Trp—Gly—OH | H—Phe—Ala—NHBzh | Z—Trp—Gly—Phe—Ala—NHBzh | 58 | 245–247 | 1 | 70.93 | 5.95 | 10.79 |
| | | | | | | 2 | 70.51 | 70.51 | 5.91 10.75 |
| 24 | Z—Leu—Ala—OH | H—Phe—Ala—NHBzh | Z—Leu—Ala—Phe—Ala—NHBzh | 38 | 259–262 | 1 | 70.07 | 6.86 | 9.73 |
| | | | | | | 2 | 69.82 | 6.78 | 9.73 |
| 25 | Z—Pro—Leu—OH | H—Phe—Ala—NHBzh | Z—Pro—Leu—Phe—Ala—NHBzh . ½H₂O | 39 | 210–213 | 1 | 70.00 | 6.94 | 2.28 |
| | | | | | | 2 | 69.44 | 6.72 | 9.20 |
| 26 | Z—Ala—Phe—OH | H—Phe—Ala—NHBzh | Z—Ala—Phe—Ala—NHBzh . ½H₂O | 57 | 256–259 | 1 | 70.84 | 6.34 | 9.18 |
| | | | | | | 2 | 70.65 | 6.19 | 9.14 |
| 27 | Z—Ala—Tyr—OH | H—Phe—Ala—NHBzh | Z—Ala—Tyr—Phe—Ala—NHBzh . H₂O | 34 | 252–253 | 1 | 68.59 | 6.27 | 8.89 |
| | | | | | | 2 | 68.17 | 6.00 | 9.11 |

Table 5

| Example | Acid component | Amine component | Product | Yield (%) | Melting point (°C) | 1 2 | Elementary Analysis calculated (%) found (%) C | H | N |
|---|---|---|---|---|---|---|---|---|---|
| 28 | Z-Ala-OH | H-Phe-Phe-OBuᵗ | Z-Ala-Phe-Phe-OBuᵗ | 71 | 160–163 | 1 | 69.09 | 6.85 | 7.32 |
| | | | | | | 2 | 69.05 | 6.87 | 7.36 |
| 29 | Z-Gln-OH | H-Phe-Phe-OBuᵗ | Z-Gln-Phe-Phe-OBuᵗ | 86 | 196–200 | 1 | 66.65 | 6.71 | 8.88 |
| | | | | | | 2 | 66.51 | 6.71 | 8.74 |

Table 5-continued

| Example | Acid component | Amine component | Product | Yield (%) | Melting point (° C) | Elementary Analysis calculated (%) [1] / found (%) [2] | | |
|---|---|---|---|---|---|---|---|---|
| 30 | Z-Thr-OH | H-Phe-Phe-OBu' | Z-Thr-Phe-Phe-OBu' | 63 | 63–68 | [1] 67.64 [2] 67.24 | 6.85 6.70 | 6.96 6.88 |
| 31 | Z-Met-OH | H-Phe-Phe-OBu' | Z-Met-Phe-Phe-OBu' | 85 | 107–108 | [1] 66.32 [2] 65.30 | 6.84 6.77 | 6.63 6.53 |
| 32 | Z-Cys(Bz)-OH | H-Phe-Phe-OBu' | Z-Cys(Bz)-Phe-Phe-OBu' | 57 | 68–80 | [1] 69.04 [2] 68.92 | 6.52 6.48 | 6.04 6.06 |
| 33 | Z-Arg(NO$_2$)-OH | H-Phe-Val-OBu' | Z-Arg(NO$_2$)-Phe-Val-OBu' | 83 | oily | [1] 58.52 [2] 58.99 | 7.06 7.09 | 14.93 14.00 |
| 34 | Z-Lys(Z)-OH | H-Phe-Val-OBu' | Z-Lys(Z)-Phe-Val-OBu' | 100 | 112–115 | [1] 66.97 [2] 66.93 | 7.31 7.30 | 7.71 7.80 |
| 35 | Z-Arg(NO$_2$)-OH | H-Leu-Phe-OBu' | Z-Arg(NO$_2$)-Leu-Phe-OBu' | 57 | 88–92 | [1] 57.63 [2] 57.50 | 7.18 6.97 | 14.26 13.99 |
| 36 | Z-Lys(Z)-OH | H-Leu-Phe-OBu' | Z-Lys(Z)-Leu-Phe-OBu' | 76 | 103–106 | [1] 67.38 [2] 67.40 | 7.45 7.43 | 7.67 7.73 |
| 37 | Z-Lys(Tos)-OH | H-Leu-Phe-OBu' | Z-Lys(Tos)-Leu-Phe-OBu' | 87 | 103–106 | [1] 63.97 [2] 61.02 | 7.25 7.20 | 7.46 7.45 |

EXAMPLE 38

In a flask, 280.2 mg (1 mmol) of Z-Gln-OH and 268.5 mg (1 mmol) of H-Phe-Phe-OBu' were suspended in 10 ml of water. A glass electrode of a pH meter was inserted into the suspension and 1/10 N NaOH was added dropwise to the suspension to adjust the pH to 6.5 to 7.0 while 100 mg of Thermoase was added to the suspension with stirring to resolve the solid component. The reaction was conducted with stirring at 38° C. for 20 hours. During the reaction, 1/10 N NaOH was added to the reaction mixture while measuring the pH of the reaction mixture with the pH meter and maintaining the pH at 6.5 to 7.0. The resulting precipitate was filtered and was sequentially washed with water, 1N HCl, water, 7% ammonia water and water and then was dried. The product was recrystallized from ethyl acetate whereby 330 mg (yield of 52.3%) of the product of Z-Gln-Phe-Phe-O-Bu' having a melting point of 197 to 200° C. were obtained.

EXAMPLE 39

In a flask, 398.5 mg (1 mmol) of Z-Phe-Val-OH and 320.4 mg (1 mmol) of H-Phe-Val-OBu' were suspended in 10 ml of water. A glass electrode of a pH meter was inserted into the suspension and 1/10 N NaOH was added dropwise to the suspension to adjust the pH to 6.5 to 7.5 while adding 100 mg of Thermoase with stirring to resolve the solid component. The reaction was conducted with stirring at 38° C. for 20 hours. During the reaction, 1/10 N NaOH was added to the reaction mixture while measuring the pH of the reaction mixture with the pH meter to maintain the pH at 6.5 to 7.5. The resulting precipitate was filtered and was sequentially washed with water, 1N HCl, water, 7% ammonia water and water and was dried. The product was recrystallized from ethyl acetate whereby 240 mg (yield of 34.2%) of the product, Z-Phe-Val-Phe-Val-O-Bu' having a melting point of 130 to 145° C. were obtained.

EXAMPLE 40

A 0.1 g amount of Prolisin and 0.1 g of an inhibitor for proteolytic enzyme (proteinase) obtained from the potato were admixed with 3 ml of tri-shydrochloric acid buffer solution (pH 7.5) containing 2 × 10$^{-3}$M of calcium acetate and then, starch was separated from the mixture. The resulting solution was added to 0.33 g (1 mmol) of Z-Gln-Gly-OH and 0.26 g (1 mmol) of H-Leu-Val-NH$_2$.HCl and then 1 ml of 1N NaOH was added to the mixture and the mixture was stirred at 38° to 40° C. for 20 hours. The resulting precipitate was filtered and was sequentially washed with 7% ammonia water, 5% citric acid and water whereby 0.394 g of crude crystals having a melting point of 237° to 240° C. and $[\alpha]_D^{23}$ = −22.0 (C=0.5 AcOH) was obtained. The product was added to methanol and the mixture was boiled and a small amount of insoluble impurity was removed whereby 0.38g (70%) of crystals having a melting point of 244° to 247° C. and $[\alpha]_D^{25}$ = −20.0 (C=0.5 AcOH) was obtained.

| Elemental Analysis C$_{26}$H$_{40}$N$_6$O$_7$ | | | |
|---|---|---|---|
| | C | H | N |
| Calculated(%) | 56.92 | 7.34 | 15.32 |
| Found(%) | 56.89 | 7.30 | 15.26 |

EXAMPLE 41

A 0.2 g amount of Prolisin and 0.2 g of an inhibitor for proteolytic enzyme (proteinase) obtained from the potato were admixed with tris-hydrochloric buffer solution (pH 7.5) containing 2 × 10$^{-3}$ M of calcium acetate and then, starch was separated from the mixture. The resulting solution was added to 0.43 g (1 mmol) of Z-Leu-Tyr-OH and 0.33 g (1 mmol) of H-Leu-Val-OMe.HBr and then 1 ml of 1N NaOH was added to the solution and the mixture was stirred at 38° to 40° C. for 20 hours. After the reaction, the reaction mixture was mixed with ethyl acetate with stirring and the water phase was removed and the organic phase was washed sequentially with 7% ammonia water, 1N HCl, an aqueous solution of saturated sodium chloride and was dried with Na$_2$SO$_4$. The mixture was concentrated whereby 0.52 g (yield of 78.8%) of a white foamy powder was obtained. The product was treated by TLC chromatography with a developer of sec-butanol-3% ammonia water (8:3) (Rf=0.85) and was recrystallized from dioxane-water whereby crystals having a melting point of 184° to 190° C. and $[\alpha]_D^{29}$ = −50.0 (C=1.0 methanol) were obtained. The data of the same product by the DCCl-HOBt method were a melting point of 176° to 181° C., $[\alpha]_D^{29}$ = −48.6 (C=1.0 methanol)

| Elemental Analysis C$_{35}$H$_{50}$N$_4$O$_8$.1/2H$_2$O | | | |
|---|---|---|---|
| | C | H | N |
| Calculated(%) | 63.33 | 7.74 | 8.44 |
| Found(%) | 63.36 | 7.70 | 8.15 |

EXAMPLES 42 to 45:

The process of Example 40 was repeated except that the acid components and the amine components and the components shown in Table 6 were used.

Table 6

| Example | Acid component | Amine component | Yield (%) | Melting point (° C) | $[\alpha]_D$ |
|---|---|---|---|---|---|
| 42 | ZLeuPheOH | HLeuLeuOMe | 65 | 190–192 | −57.2 (C = 0.5, MeOH) |
| 43 | pMZMetGlyOH | HPheNH$_2$ | 82 | 226–229 | −1.0 (C = 0.25, DMF) |
| 44 | ZPheOH | HLeuOme | 79 | 104–106 | −10.0 (C = 0.5, EtOH) |
| 45 | ZMetOH | HLeuPheObu · t | 82 | 160–163 | −39.0 (C = 1, MeOH) |

EXAMPLE 46

A mixture of 715 mg (2.00 mmol) of N-benzyloxycarbonyl (β-benzyl)-D,L-aspartic acid, 215 mg (1.00 mmol) of L-phenyl-alanine methyl ester hydrochloride and 20 mg of a purified Thermoase and 20 mg of an inhibitor for proteolytic enzyme obtained from the potato was admixed with 10 ml of tris-hydrochloric acid buffer solution (pH 8.0) containing 2.0 × 10$^{-2}$ M of calcium acetate and then 1N NaOH was added to the mixture to adjust the pH to 7.5. The reaction was conducted with stirring at 39° C. for 17 hours. The resulting white precipitate was filtered and was sequentially washed with 5% ammonia water, 5% aqueous citric acid solution and water and was dried whereby 413 mg of N-benzyloxycarbonyl-(β-benzyl)-L-aspartyl-L-phenylalanine methyl ester were obtained. The product was recrystallized from ethylacetate-petroleum ether.

| yield | 79.6% | | |
|---|---|---|---|
| melting point | 116 to 117° C | | |
| $[\alpha]_D^{20}$ = −12.2 (C = 1.0 dimethylformamide) | | | |
| Elemental Analysis | C$_{29}$H$_{30}$N$_2$O$_7$ | | |
| | C | H | N |
| Calculated (%) | 67.17 | 5.83 | 5.40 |
| Found(%) | 67.35 | 5.81 | 5.28 |

EXAMPLE 47

The process of Example 1 was repeated except that 715 mg of N-benzyloxycarbonyl-(β-benzyl)-D,L-aspartic acid, 431 mg of D,L-phenylalanine methyl ester hydrochloride, and 20 mg of Thermolysin were reacted without using an inhibitor. As a result, 244 mg (yield of 47.0%) of the same product was obtained.

EXAMPLE 48

The process of Example 1 was repeated except that 357 mg (1.00 mmol) of N-benzyloxycarbonyl-(β-benzyl)-L-aspartic acid, and 431 mg (2.00 mmol) of D,L-phenylalanine methyl ester hydrochloride were used. As a result, 426 mg (yield of 82.1%) of N-benzyloxycarbonyl-(β-benzyl)-L-aspartyl-L-phenylalanine methyl ester having an $[\alpha]_D^{25}$ = −12.5(C=1.0 dimethylformamide) were obtained.

EXAMPLE 49

The process of Example 1 was repeated except that 715 mg (2.00 mmol) of N-benzyloxycarbonyl-(β-benzyl)-D,L-aspartic acid and 413 mg (2.00 mmol) of D,L-phenylalanine methyl ester hydrochloride were obtained. As a result, 410 mg (yield of 79.0%) of N-benzyloxycarbonyl-(β-benzyl)-L-aspartyl-L-phenylalanine methyl ester having an $[\alpha]_D^{20}$ = −12.0 (C=1.0 dimethylformamide) were obtained.

EXAMPLE 50

A 100 mg amount of Thermoase and 100 mg of an inhibitor for proteolytic enzyme obtained from the potato were admixed with 10 ml of tris-hydrochloric acid buffer solution (pH 8.0) containing 2.0 × 10$^{-2}$ M of calcium acetate. The mixture was stirred at 30° C. for 10 minutes. The insoluble material was removed by filtering the solution through a glass filter (G-3). The filtrate was mixed with 715 mg (2.00 mmol) of N-benzyloxycarbonyl-(β-benzyl)-D,L-aspartic acid and 215 mg (1.00 mmol) of L-phenylalanine methyl ester and then 1N NaOH was added to the filtrate to adjust the pH to 7.5. The reaction was carried out with stirring at 39° C. for 17 hours. The resulting white precipitate was treated in accordance with the process of Example 1 whereby 411 mg (yield of 79.2%) of N-benzyloxycarbonyl-(β-benzyl)-L-aspartyl-L-phenylalanine methyl ester having an $[\alpha]_D^{23}$ = −12.5 (C=1.0 dimethylformamide)

EXAMPLE 51

The process of Example 50 was repeated except that 715 mg (2.00 mmol) of N-benzyloxycarbonyl-(β-benzyl)-D,L-aspartic acid and 215 mg of L-phenylalanine methyl ester hydrochloride, 200 mg of Prolisin and 200 mg of the inhibitor were reacted. As a result, an 110 mg amount (yield of 21.2%) of N-benzyloxycarbonyl-(β-benzyl)-L-aspartyl-L-phenylalanine methyl ester having an $[\alpha]_D^{22}$ = −12.8 (C−1.0 dimethylformamide) was obtained.

EXAMPLE 52

The process of Example 51 was repeated except that 357 mg (1.00 mmol) of N-benzyloxycarbonyl-(β-benzyl)-L-aspartic acid and 431 mg (2.00 mmol) of D,L-phenylalanine methyl ester hydrochloride were reacted. As a result, a 238 mg amount (yield of 45.8%) of N-benzyloxycarbonyl (β-benzyl)-L-aspartyl-L-phenylalanine methyl ester having an $[\alpha]_D^{20}$ = −13.2 (C=1.0 dimethylformamide) was obtained.

EXAMPLE 53

The process of Example 51 was repeated except that 715 mg (2.00 mmol) of N-benzyloxycarbonyl-(β-benzyl)-D,L-aspartic acid and 431 mg (2.00 mmol) of D,L-phenylalanine methyl ester hydrochloride were obtained. As a result, a 121 mg amount (yield of 23.3%) of N-benzyloxycarbonyl-(β-benzyl)-L-aspartyl-L-phenylalanine methyl ester having an $[\alpha]_D^{26}$ = −12.4 (C=0.5 dimethylformamide) were obtained.

EXAMPLES 54 to 60

The process of Example 46 was repeated under the conditions stated in Table 7. As a result, the product of Example 46 was obtained.

Table 7

| Example | N-benzyl oxycarbonyl (α-benzyl)-aspartic acid (Amount mg) | Phenyl alanine methyl ester (Amount mg) | Proteinase (Amount mg) | Inhibitor (Amount mg) | Yield (%) |
|---|---|---|---|---|---|
| 54 | D,L-compound (715) | L-compound (215) | Thermolysin (20) | — | 47.0 |
| 55 | L-compound (357) | D,L-compound (413) | " | — | 86.1 |
| 56 | L-compound (357) | D,L-compound (431) | Crude Thermoase (100) | Potato inhibitor (100) | 75.5 |
| 57 | D,L-compound (715) | D,L-compound (431) | " | " | 48.4 |
| 58 | D,L-compound (715) | L-compound (215) | Purified Thermoase | — | 63.6 |
| 59 | L-compound (357) | D,L-compound (431) | " | — | 36.2 |
| 60 | D,L-compound (715) | D,L-compound (431) | " | — | 21.8 |

EXAMPLES 61 to 74

The process of Example 46 was repeated except that the acylamino acids and the amino acid derivatives set forth in Table 8 were used. The results are shown in Table 8. All of the products were L,L-products.

Table 8

| Example | Acyl amino acid | Amino acid derivative | Product | Yield (%) | $[\alpha]_D$ |
|---|---|---|---|---|---|
| 61 | Z-L-AlaOH | D,L-H-PheOMe . HCl | Z-L-Ala-L-PheOMe | 23.2 | −14.5 (C=0.5, MeOH) |
| 62 | Z-D,L-AlaOH | L-H-PheOMe . HCl | " | 23.7 | " |
| 63 | Z-D,L-AlaOH | D,L-H-PheOMe . HCl | " | 13.8 | " |
| 64 | pmZ-L-TrpOH | D,L-H-PheOMe . HCl | pmZ-L-Trp-L-PheOMe | 52.3 | −37.0 (C=1, DMF) |
| 65 | pmZ-D,L-TrpOH | L-H-PheOMe . HCl | " | 67.4 | " |
| 66 | pmZ-D,L-TrpOH | D,L-H-PheOMe . HCl | " | 39.7 | " |
| 67 | Boc-L-LeuOH | D,L-H-PheOMe . HCl | Boc-L-Leu-L-PheOMe | 19.6 | −26.4 (C=0.5, MeOH) |
| 68 | Boc-D,L-LeuOH | L-H-PheOMe . HCl | " | 19.9 | " |
| 69 | Z-L-PheOH | D,L-H-PheOMe . HCl | Z-L-Phe-L-PheOMe | 71.2 | −17.6 (C−1, DMF) |
| 70 | Z-D,L-PheOH | L-H-PheOMe . HCl | " | 47.8 | " |
| 71 | Z-D,L-PheOH | D,L-H-PheOMe . HCl | " | 27.2 | " |
| 72 | Z-L-Asp(BZL)OH*1 | D,L-H-PheOEt HCl | Z-L-Asp(BZL)-L-PheOEt | 84.0 | −12.2 (C=1, DMF) |
| 73 | Z-D,L-Asp(BZL)OH | L-H-PheOEt . HCl | Z-L-Asp(BZL)-L-PheOEt | 79.2 | " |
| 74 | Z-D,L-Asp(BZL)OH | D,L-H-PheOEt . HCl | Z-L-Asp(BZL)-L-PheOEt | 70.3 | " |

*1 : BZL: α-benzyl ester

Having now fully described the invention, it will be apparent to one of ordinary skill in the art that many changes and modifications can be made thereto without departing from the spirit or scope of the invention as set forth herein.

What is claimed as new and intended to be secured by letters patent is:

1. A process for producing a peptide having the formula:

X—A—B—Y wherein A and B are the same or different and each represents an amino acid residue or a peptide residue, X represents an amino acid protective group, Y represents a carboxyl protective group, which comprises:

reacting an acid component of an amino acid or peptide having an N-terminal protective group or a salt thereof which has the formula

X—A—OH with an amine component of an amino acid or peptide having a C-terminal protective group or a salt thereof which has the formula

H—B—Y in the presence of a metalloproteinase enzyme produced from microorganisms in an aqueous solution having a pH necessary to maintain the activity of said metalloproteinase enzyme;

wherein the combination of said acid component (I) and said amine component (II) is selected from the group consisting of L−I+DL−II, DL−I+L−II, and DL−I+DL−II.

2. The process of claim 1, wherein said acid component is an acyl amino acid (I) and said amine component is an amino acid derivative (II) and said components are reacted as shown in the following equation:

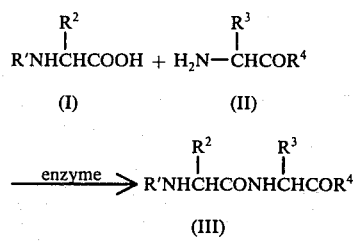

wherein R' represents acyl, $R^2$ represents a side chain group of an α-amino acid, $R^3$ represents a side chain group of an α-amino acid and $R^4$ represents a protective group for the carboxyl group.

3. The process of claim 1, wherein an inhibitor for the proteolytic enzyme extracted from oats, fava, kidney beans or potato is added to said aqueous solution.

* * * * *